United States Patent [19]

Di Luccio et al.

[11] Patent Number: 4,720,384
[45] Date of Patent: Jan. 19, 1988

[54] MANUFACTURE OF HOLLOW FINE TUBULAR DRUG DELIVERY SYSTEMS

[75] Inventors: Robert C. Di Luccio, Wilmington, Del.; Ray B. Duggins, Chadds Ford; Eli Shefter, Media, both of Pa.

[73] Assignee: E. I. Du Pont de Nemours and Company, Wilmington, Del.

[21] Appl. No.: 898,653

[22] Filed: Aug. 21, 1986

Related U.S. Application Data

[63] Continuation-in-part of Ser. No. 730,064, May 3, 1985, Pat. No. 4,673,565.

[51] Int. Cl.$^4$ .................... A61K 31/74; B29C 47/04; B29C 63/18
[52] U.S. Cl. ........................... 424/78; 264/41; 264/150; 264/171; 264/177.14; 264/204; 264/209.1; 264/211.14; 264/344; 264/561; 264/562; 424/468; 424/486; 424/501; 604/892.1
[58] Field of Search ............ 264/41, 150, 171, 177.14, 264/177.15, 204, 205, 209.1, 209.3, 211.14, 344, 561, 562; 424/78, 468, 486, 501; 604/892

[56] References Cited

U.S. PATENT DOCUMENTS

| | | | |
|---|---|---|---|
| 2,987,445 | 6/1961 | Levesque | 264/340 X |
| 3,832,252 | 8/1974 | Higuchi et al. | 424/486 X |
| 3,854,480 | 12/1974 | Zaffaroni | 604/892 |
| 3,923,969 | 12/1975 | Baukal et al. | 424/468 |
| 3,946,106 | 3/1976 | Chien et al. | 424/425 |
| 4,017,030 | 4/1977 | Coplan et al. | 239/44 |
| 4,024,871 | 5/1977 | Stephenson | 128/335.5 |
| 4,053,546 | 10/1977 | Yamasaki et al. | 264/171 X |
| 4,175,326 | 11/1979 | Goodson | 424/435 X |
| 4,205,060 | 5/1980 | Monsimer et al. | 424/78 X |
| 4,237,885 | 12/1980 | Wong et al. | 604/892 |
| 4,344,431 | 8/1982 | Yolles | 604/892 X |
| 4,404,183 | 9/1983 | Kawata et al. | 424/78 X |
| 4,490,322 | 12/1984 | Zierenberg | 264/205 |
| 4,525,340 | 6/1985 | Lange et al. | 428/315.5 X |

FOREIGN PATENT DOCUMENTS

| | | | |
|---|---|---|---|
| 0061192 | 3/1982 | | |
| 76442 | 4/1983 | European Pat. Off. | 264/561 |

*Primary Examiner*—Jeffery Thurlow
*Assistant Examiner*—Leo B. Tentoni

[57] ABSTRACT

Pharmaceutical compositions are provided which contain hollow fine tube drug delivery systems. The compositions comprise a pharmaceutically suitable carrier, preferably in the form of a capsule, tablet, suspension, or suppository, and at least one drug delivery system which consists essentially of (1) a polymeric tube having a membrane outer sheath and a hollow core, and (2) at least one drug compound contained within the core, said system contained in the composition in an amount sufficient to deliver a therapeutic amount of the drug contained therein at a predetermined rate over a predetermined period of time. By varying the polymer, the permeability of the outer sheath, the drug, the drug concentration in the hollow core of the tube, the tube diameter, the tube length, the tube core diameter, and the sealing of the tube ends, a wide variety of drug therapeutic amounts, rates and dosing times can be achieved.

21 Claims, No Drawings

MANUFACTURE OF HOLLOW FINE TUBULAR DRUG DELIVERY SYSTEMS

RELATIONSHIP TO OTHER APPLICATIONS

This application is a continuation-in-part of copending U.S. Application Ser. No. 730,064, filed May 3, 1985, now U.S. Pat. No. 4,673,565.

BACKGROUND OF THE INVENTION

1. Field of Invention

This invention relates to pharmaceutical compositions and more particularly to controlled release pharmaceutical compositions containing hollow tube drug delivery systems.

2. Prior Art:

Controlled delivery or sustained release formulations have gained wide popularity in the pharmaceutical industry. The popularity of these formulations has grown due to the usefulness in extending the utility of particular drugs which require specific dosages and delivery of the dosage at a non-toxicological rate.

In the pharmaceutical industry, sustained release has been used extensively for oral medications over a number of years. Sustained release formulations include encapsulated pellets or beads, enteric coated formulations, use of slightly soluble salts, drug complexes, and porous tablets containing dispersed drugs.

Controlled drug delivery on the other hand is aimed at achieving sustained release of a drug at a constant rate (zero order) for long periods of time. Zero order release can be provided at the present time only by mechanical pumps, such as automatic syringes and implantable pumps, osmotic pumps such as Alza's systems known as Alzet®, Progestasert® and Ocusert®, chemically controlled biodegradable mechanisms, and diffusional systems based on polymeric membranes and matrices such as the currently marketed transdermal systems for the delivery of nitroglycerin for angina pectoris and scopolamine for motion sickness.

Solid fibers have been used in sutures encapsulated with antibiotics and in intrauterine devices to release hormones.

While much work has been done over many years relating to the sustained release and the controlled release of drugs, there still is a need for new systems that are capable of delivering a predetermined amount of a drug at a predetermined rate, over a selected time. The present invention provides such systems.

BRIEF DESCRIPTION OF THE DRAWINGS

FIG. 1 schematically illustrates a procedure for preparing hollow tubes having drugs incorporated in the cores of the tubes via solutions of the drugs.

FIGS. 2 and 3 illustrate procedures involving membrane formation by utilization of density gradients. If the bath density is less than the tube, the tube will sink and collect at the bottom of the bath (FIG. 2). If the bath density is greater, the spinning device is inverted and the tube will float upward and collect at the top of the phase inversion stage (FIG. 3).

SUMMARY OF THE INVENTION

According to the present invention there is provided a process for preparing a hollow tube drug delivery system comprising:

a. extruding a polymer solution or suspension through an annular orifice to provide a tubular membrane having a hollow core;

b. simultaneously extruding a drug suspended in a polymer solution into the hollow core of the tubular membrane to provide a drug encapsulated tubular membrane system;

c. passing the system into a non-solvent for the polymers having a density different from that of the system, to coagulate the polymers under conditions to minimize orientation in the tube polymer and to create pores in the tube polymer wall;

d. removing residual solvent from the system; and e. collecting a drug encapsulated, porous polymeric hollow tube.

According to a preferred embodiment, a plurality of hollow, porous, segmented polyurethane/urea tubes up to 15 cm in length, preferably about 0.5 mm to about 2 cm, containing at least one drug in the core are mixed with a suitable pharmaceutical carrier for oral administration.

DETAILED DESCRIPTION OF THE INVENTION

The preparation of hollow tubes from polymers can be achieved by various routes. These are referred to as wet, dry or melt-forming processes. Melt-forming involves heating a polymer above its melting point and extruding it through an orifice (usually referred to as a die) which is designed to form a hollow tube. Once extruded, the melt is cooled via a quench which allows the polymer to solidify into a fine tube. In the dry-forming process, a solution of the polymer is extruded through a desired orifice and is fed into a heated column which allows for evaporation of the solvent and subsequent formation of a tube. In a wet-membrane forming process, a solution of the polymer is extruded though an orifice and quenched in a non-solvent for the polymer resulting in coagulation of the polymer to a tube. Of the above mentioned forming processes, wet-membrane forming allows one to easily produce hollow porous tubes. It will be appreciated that the particular forming process used will be dependent upon the polymer used and type of hollow tube desired.

To make a membrane outer sheath in a hollow tube, one first dissolves or disperses a polymer to form a liquid solution. A porous membrane results when the latter process is reversed under controlled condition. The polymer coagulates into a continuous matrix as it separates from the solvent which forms a dispersion of droplets. As the polymer solidifies and the solvent is extracted, the dispersion of droplets becomes a network of open pores. This phase inversion or separation can be achieved by a number of techniques. In one, the temperature of the polymer solvent dictates the point at which the phase inversion occurs. In another, the polymer solvent is physically exchanged with a poor solvent for the polymer causing phase inversion.

The size of the pores is affected by the solvent strength of a polymer. A rapid decrease in solvent strength often tends to entrap a dispersion of small droplets within the continuous polymer phase. A slow decrease in solvent strength allows for nucleation sites within the polymer matrix allowing for formation of larger pores. In this case, the reduction in solvent strength must be rapid enough to allow for the structure of the membrane to set.

Another way to change porosity and volume of the porous network in the polymer is to change the concentration of the polymer solution. Lower concentrations have a tendency to promote larger pores and greater pore volume. However, there is a limit to how high (usually no more than 45% w/w) the polymer concentration can be in a solvent, otherwise, the polymer will become the dispersed phase in a continuous solvent phase, thereby eliminating the porous network. Another method to achieve porous tubular membranes is to cause a rapid phase inversion of the polymer solution by cooling.

Generally, as the polymer membrane of the hollow tube is quenched, the surface of the polymer tends to have a "dense" skin due to a rapid reduction of solvent strength at the surface. The interior, on the other hand, must have the solvent diffuse and migrate through the polymer matrix. This results in larger interior pores. In a thermally induced quench, the relative cooling rates can determine the relative degree of porosity.

Conventional machinery used in the manufacture of tubes often has a tendency to orient the polymer by either the mechanical features of the device or by the influence of gravity. This often results in distortion of pore shape and orientation in tubular membrane production and also requires that the solution have inherent physical properties enabling it to be processed on the conventional equipment. Hot and cold drawing can also be used to vary the outside diameter of the tube and its core volume. For example, a large diameter tube can be extruded and then drawn down to a small diameter.

In order to minimize the effects of orientation and maximize the benefits of uniform porosity and allow for production of membranes from fragile polymer systems, a preferred tube forming process called density gradient membrane formation is used. This process uses density gradients in the phase inversion bath. Careful selection of the coagulation solutions allows one to use gravity to gently draw and collect the thin tubular membrane in the phase inversion bath. The density gradient of the coagulation solution can be established by either multiple stacked layers of liquids with different densities, or by the use of a single coagulant subjected to a temperature gradient which in turn produces a density gradient. Proper selection of the coagulation solution is extremely important when processing delicate membranes. Depending on the density of the tube vs. the quench bath, it can be spun either upwards or downwards. For drug encapsulation, selection of the quench media is dependent on the drug solubility and miscibility of the solvent for the polymer.

In order to encapsulate a drug compound in the core of the hollow tube, either a suspension, solution, or other extrudable form of the compound has to be prepared initially. This is achieved by selecting a solvent for the drug and dissolving it to a desired concentration or by melting the drug material to be encapsulated. Alternatively, a suspension of fine particles of drug in an appropriate liquid medium is prepared which can either be heated to form a liquid suspension that can be solidified in the core of the tube or can be made viscous enough for the drug to remain in suspension. Often a dilute solution of the polymer used to make the tubular membrane outer sheath serves as an adequate suspending medium for the drug. Once the appropriate drug solution or suspension is made, it is pumped into the annular die simultaneously with the solution of the polymer forming the outer sheath of the hollow tube. This is schematically illustrated in FIG. 1. The resulting hollow tube containing the drug is quenched in an appropriate poor solvent for the polymer and the drug and is permitted to set in the quench bath. If necessary, the tube can be removed from the initial quench and placed in another solvent which can expedite removal of the remaining solvent in the tube, without removing the drug. For example, a volatile non-solvent for the drug and tube can be used to exchange with any residual solvent remaining in the tube and subsequently be removed by vacuum extraction.

After the drug encapsulated hollow tube is formed, the continuous tube is cut into lengths suitable for formulation into a pharmaceutical composition for administration to mammals, particularly in the form of a tablet, capsule, suppository, suspension, or suture. The length of the hollow tube can be as long as can conveniently be formulated into a dosage form commensurate with the delivery of a therapeutic amount of the encapsulated drug. Formulations can be prepared making use of carriers, vehicles, diluents, excipients, and procedures well known to those skilled in the pharmacy art.

For example, the hollow tubular delivery system can be one continuous length that can be "balled up" into a dosage form. The continuous tube may be more suitable for the slow release of a drug over a long period of time via an osmotic pump delivery system. In this delivery system, at least one of the tube ends is open and the membrane outer sheath is impermeable to water and the drug, i.e., the drug is delivered out the end of the tube. Release rates can be increased by making the membrane outer sheath permeable or semi-permeable.

Preferred pharmaceutical compositions contain a plurality of drug encapsulated hollow tubes. These tubes can be of uniform length or of different lengths with the ends either open or sealed. By varying the lengths of the tubes, openness of the ends, and permeability of the membrane outer sheath, the rate and time of delivery can be varied and be predetermined. Tube lengths up to 15 cm are preferred; however, shorter lengths are more preferred, e.g., the tubes are preferably less than 2 cm long, preferably in the range of less than about 0.5 mm to about 2 cm, and most preferably in the range of about 0.5 mm to about 6 mm. The tubes can have both ends open, both ends sealed, or one end open and one end sealed.

The hollow tubes preferably have a small diameter for ease of formulation. While final diameters can be as high as 5 mm, it is preferred that they be about 0.5 mm in outside diameter or less. Larger diameter tubes can be spun and then drawn down to a smaller diameter. Aspect ratios (ratio of length to diameter) of the tubes will generally be in the range of about 1 to 30. The core diameters of the hollow tubes typically range from about 25-90% of the outside diameter, preferably about 40-85%.

The drug concentration in the core of the tube depends upon many variables and will be loaded to provide the best delivery rate and time span for the particular drug involved. Drug concentration can vary over a wide range, i.e., about 1-90% by weight of the total weight of the tube and compound; however, it is preferred that the drug concentration be in the range of about 5-75% by weight.

The drug in the core can be mixed with a pharmaceutically suitable salt or sugar to increase the dissolution of the drug in the core. This is particularly appropriate where the tube acts as an osmotic pump since the salt or sugar assists in forcing water into the core. While magnesium sulfate is a preferred salt, other useful salts are any water-soluble, divalent or monovalent salts.

A hollow tube that has been found particularly suitable for pharmaceutical formulations is a segmented polyurethane/urea tube free of additives having an outside diameter of less than 0.5 to about 1.5 mm, a core volume of about 60–90%, a length of about 3–6 mm and a drug concentration in the range of about 25–75% by weight. The membrane outer sheath of these tubes is porous, and had a porosity of 500 daltons or more, determined by dye penetration tests.

The material of choice for production of the hollow tube depends on the characteristics one would like to have in the final product. They can be chosen for ease of membrane fabrication, hydrophilicity, elasticity, molecular weight, biocompatibility, degree of porosity, processing temperature, and compatibility with the drug being encapsulated. Polymers which can be used include polyolefins such as polypropylene, polyurethanes such as segmented polyurethane/ureas, ethylene-vinyl acetate copolymers having a vinyl acetate content of at least 33% by weight, polyvinyl alcohols, and blends of water-soluble polymers with some of the aforementioned polymers.

Polypropylene can be used for the production of fine hollow tubular membranes with wide variations in porosity. They are normally melt formed at temperatures above 200° C. but they can also be dissolved in solvents at elevated temperatures and then quenched. Because of the high temperatures necessary for the fabrication of polypropylene hollow tubes, care must be used in selecting drugs which are not heat sensitive. Alternatively, the drug can be injected into the core of the hollow tube after it is formed; however, such a procedure is not preferred.

Polyurethanes, such as segmented polyurethane/ureas sold under the name Lycra ®, can be dissolved at ambient temperature in dimethylacetamide (DMAC) or other appropriate solvent and fabricated into porous, hollow tubes at ambient temperature. They can also be blended easily with water-soluble materials such as polyvinylpyrrolidone (PVP), polyethylene glycol (PEG), and salts which enhance porosity and wettability of the resulting tubular membranes. These tubes have high elasticity, are biocompatible, and offer great flexibility in the design of hollow tubular membranes, especially by the preferred density gradient membrane formation technique. Copolymers of ethylene-vinyl acetate with at least 33% by weight of vinyl acetate can be dissolved at ambient temperature in tetrahydrofuran (THF) and fabricated into porous hollow tubes. They are easily blended with water soluble materials such as PVP, PEG, and salts. These tubular membrane systems are somewhat elastic, are biocompatible, and are easily formed into hollow tubes. Hytrel ®, a polyester elastomer, can also be formed into porous tubular membranes and blended with water-soluble polymers.

Polyvinyl alcohols can be dissolved easily in hot water at 60° C. and can be fabricated into porous hollow tubes at ambient temperatures. Because of their solubility in water, they can be used as slowly erodible matrixes for delivery of active ingredients.

Any therapeutically active drug compound can be used. In the examples which follow, the following compounds were chosen as models because of their broad range of chemical and pharmacological characteristics:

Phenylpropanolamine hydrochloride, a decongestant, pKa (base)=9.5, is freely soluble in water (25° C.).

Theophylline, an antiasthma drug, pKa (base)=0.36 with a solubility in water of 1 gram in 120 mls (25° C.).

Chlorpheniramine maleate, an antihistamine, pKa (base)=8.99, has a solubility of 1 gram in 3.4 ml water (25° C.).

Salicylic acid, a topical antiseptic, pKa=2.97, is slightly soluble in water.

Indomethacin, an antiinflammatory drug, pKa (acid)=4.5, has a low solubility in water.

Nalbuphine hydrochloride, an analgesic, pKa (base)=8.4, is soluble in water.

In the Examples which follow, hollow tubes were prepared by one of two procedures which can be varied depending upon the end results desired. Drugs were incorporated in the cores of the tubes via solutions or suspensions of the drugs.

PROCEDURE A

This procedure uses the arrangement shown in FIG. 1. In this procedure, a solution of the polymer for the outer membrane sheath is pumped through the annular die simultaneously with a solution of the core material which results in a tubular membrane surrounding core solution. This is passed through an annular die (O.D.=2.18 mm) into a quench tube containing 1 liter of a coagulant for the polymer. The solvent is continuously removed from the polymer/drug encapsulated system and it is collected in a rotating piddle pot. The loaded tube remains in the piddle pot as the solvent is being removed and is removed after solvent removal is nearly complete for further treatment, e.g., removal of trace amounts of solvent. The tube is formed at a rate of 0.1 to 2 cm³/min and the speed of the piddle pot is the same as the speed of the tube as it exits the quench tube. Temperature of spinning and coagulation are controlled by heating mantles surrounding the die and coagulation kettle.

Table I gives Examples of drug loaded tubes which were formed by the above method. All runs were conducted at room temperature.

PROCEDURE B

This procedure involves membrane formation by utilization of density gradients. This procedure is desirable for most applications where membrane fabrication and drug encapsulation are involved. Due to excessive "draw" which is inherent in most extrusion techniques and also to the difficulty of fabricating slow forming membranes or tubes whose polymer structure has weak physical characteristics, this procedure allows for membrane formation of polymers having any or all of the characteristics mentioned. By correctly choosing coagulants with a density slightly different than that of the polymer/drug encapsulated tube, one can use gravity to gently draw and collect a forming tube within the phase inversion bath (coagulant). If the bath density is less than the tube, the tube will sink and collect at the bottom of the bath (FIG. 2). If the bath density is greater, the spinning device is inverted and the tube will float upward and collect at the top of the phase inversion stage (FIG. 3). This procedure can use several bath fluids of decreasing density stacked vertically in the tube allowing for flexibility in design to give the ability to use a sequence of quench-coagulation treatments in the same phase inversion unit. For example, a layer of a heavy liquid can be placed adjacent to the die for thermal insulation. A lighter heat conductive liquid on top of this layer becomes the quenching agent.

The encapsulation of drugs is accomplished by dissolving or suspending the drug in a suitable liquid, or melting the drug, then taking this drug preparation and loading it into a stainless steel piston used for inserting the core material. A second piston for the outer sheath membrane contains the polymer solution. Temperature control, if necessary, of the pistons, die, and coagulant is accomplished by heating jackets. Die size is chosen depending on the diameter of the tube desired, and on the lumen desired. The rate at which the polymer and drug is pumped is controlled by settings on the pumps. The gap between the die and the top of the coagulation bath, where appropriate, is set according to the amount of "draw down" desired. This procedure is more fully described by the following:

The porous, polymeric hollow tube is formed by extruding a tubular membrane from a polymer solution or suspension and then passing the tubular membrane into a coagulation bath which is a non-solvent for the polymer. Simultaneously with the extrusion of the hollow tube, a drug suspension (drug suspended in a polymer solution) is extruded at the same rate as the tube extrusion into the hollow core of the tubular membrane to form a drug encapsulated tubular membrane system. In the coagulation bath the solvent is removed from the system via phase inversion, during which the pores in the polymer wall are formed. After removal from the coagulation bath, residual solvent is removed, and the drug encapsulated, porous, polymeric hollow tube is collected, e.g., on a take-up roll. From the take-up roll, the collected drug-filled tube is cut into desired lengths, ends sealed as desired, and a plurality of the cut tubes are mixed with a suitable pharmaceutical carrier for oral administration.

The polymer solution which forms the porous, tubular membrane is preferably a solution of about 15–40% (preferably 30–40%) by weight of a segmented polyurethane/urea derived from polyether soft segments (Lycra®) and free of additives and dissolved in dimethylacetamide (DMAC) or N-methylpyrrolidone (NMP), preferably DMAC. Another useful polymer solution is a solution of about 15–25% by weight of a polylactide having a number average molecular weight of about 100,000 to 500,000 in NMP, DMAC or a chlorinated solvent such as chloroform, or methylene chloride. The polylactide can be formed from polymerization of lactic acid. A further useful polymer solution is a solution of about 15–25% by weight of polyvinyl alcohol in water. The polyvinyl alcohol is a homopolymer which is a fully hydrolyzed polyvinyl acetate (with about greater than 99.8% of the acetate groups converted to alcohol groups) or a partially hydrolyzed polyvinyl acetate with up to about 25% of residual vinyl acetate groups. In addition, the polyvinyl alcohol can be a copolymer with an acrylic monomer such as methyl acrylate.

While the above polymers are preferred, any polymer can be used that is soluble in water or an organic solvent up to a concentration in the solvent of about 40% by weight. Other such polymers include ethylcellulose, hydroxypropylcellulose, hydroxypropyl methylcellulose, ethylene/vinyl acetate, and cellulose acetate.

The drug suspension extruded into the hollow core of the tubular membrane can be a suspension of any drug in a polymer solution either the same as or different from the polymer solution used to prepare the hollow tubular membrane. Drugs are usually solids and a solid drug in powder form is preferred. Preferred polymer solutions are propylene glycol, polyethylene glycol having a molecular weight greater than 400 (preferably in the range of about 400–5000), about 1–12% by weight of a segmented polyurethane/urea derived from polyether soft segments, and about 1–5% by weight of polyvinyl alcohol in water. Other polymer solutions can be used such as sodium carboxymethylcellulose, hydroxypropyl cellulose, and hydroxypropylmethyl cellulose. Typically, the drug will comprise about 3–50% by weight in the polymer solution.

The coagulation bath for the extruded system is composed of a non-solvent for the polymer used for the tubular membrane. This is preferably water, an alkyl alcohol of 1–3 carbon atoms (preferably methanol or ethanol, or a mixture of the two). Other useful non-solvents are acetone, ether, and aqueous solutions of sodium sulfate, or sodium hydroxide. As stated earlier, the density of the non-solvent is different from the extruded system so that the system either rises to the top of the bath or, as preferred, sinks slowly to the bottom of the bath prior to removal and collection. A small difference in densities minimizes orientation in the tubular polymer wall and allows the creation of uniform pores in the tube wall during phase inversion.

The temperatures for extrusion and for the coagulation bath are preferably about the same but can be different depending upon the properties desired in the final product. Preferred temperatures are about room temperature; however, the temperature for the extrusions and for the coagulation bath can be independently in the range of about 15° to 180° C., depending on the heat stability of the polymer. To increase the pore size in the tubular polymer wall, the temperature can be increased to the high end, i.e., in the range of about 60° to 180° C.

Slight draw-down can be made in the extruded system to narrow the outside diameter of the final product. This is accomplished by driving the take-up roll, when extruding upward, at a slight higher speed as is well-known in the art. In the preferred downward extrusion, an airgap is provided between the die and the bath so as to give a slight neck-in. This gap can vary between 0 and a few inches, depending on the properties desired in the final product.

After removal from the coagulation bath, residual solvent is removed from the drug encapsulated, porous, polymeric hollow tube preferably by heat or by passing the product through a vacuum. The final product, having an outside diameter of about 0.5–10 millimeters, preferably about 0.5–5 millimeters is collected for subsequent processing and use.

In Tables I and II are given the conditions and characteristics of the tubes prepared using this procedure. All parts and percentages are by weight.

The following abbreviations are used in the tables:

| | Polymers and solvents: |
|---|---|
| Ur126 = | Segmented polyurethane/urea (50,000 molecular weight) |
| PVP-15 = | Polyvinylpyrrolidone (15,000 molecular weight; 40 = 40,000 molecular weight) |
| PEG = | Polyethylene glycol (400 molecular weight; 740 molecular weight; 1000 molecular weight; 1300 molecular weight; 3350 molecular weight) |
| PG = | Propylene glycol |
| EVA = | Copolymer of ethylene-vinyl |

-continued

| | |
|---|---|
| | acetate with 33% by weight vinyl-acetate (melt index 43, density 0.95 g/cc) |
| NMP = | 1-Methyl-2-pyrrolidone |
| DMAC = | Dimethylacetamide |
| THF = | Tetrahydrofuran |
| Dowex = | Dowex 50 cross-linked sulfonated polystyrene ion exchange resin |
| | Drugs |
| Sal. Acid = | Salicylic acid |
| PPA = | Phenylpropanolamine hydrochloride |
| CM = | Chlorpheniramine Maleate |
| Nalb—HCl = | Nalbuphine hydrochloride |
| Theo = | Theophylline |
| Ind = | Indomethacin | specified amount of drug encapsulated tubes and an appropriate dissolution medium (0.1N HCl, pH 7.4 phosphate buffer, buffered saline or water). This vessel is stirred at a constant rate (25, 50 or 100 rpm) for the duration of the dissolution procedure and its contents are sampled periodically to determine the amount of drug released.

The second procedure, sometimes referred to as the rotating bottle method, uses sealed, cylindrical glass tubes immersed in water at 30° C. or 37° C. and filled with drug encapsulated tubes and an appropriate dissolution medium as described above. The glass tubes are tumbled at a specified rate (15 rpm) throughout the test and the contents are sampled periodically to determine the amount of drug released. The length of the tests

TABLE I
Hollow Thin Tubular Membrane Preparation With Encapsulated Drugs

| Ex. No. | Polymer (Solvent) | Core % in Susp. or Soln. | Airgap (Inches) | Direction of Membrane Formation | Quench |
|---|---|---|---|---|---|
| 1 | 36% Ur126 (DMAC) | 3% Theo in PG | 0 | A | $H_2O$ |
| 2 | 36% Ur126 (DMAC) | 10% Sal. Acid in PG | 0 | A | $H_2O$ |
| 3 | 36% Ur126 (DMAC) | 3% Theo in PG | 0 | A | $H_2O$ |
| 4 | 36% Ur126 (DMAC) | 30% Sal. Acid in PEG 740 | 0 | A | $H_2O$ |
| 5 | 36% Ur126 (DMAC) | 30% Sal. Acid in PEG 1000 | 0 | A | $H_2O$ |
| 6 | 36% Ur126 (DMAC) | 30% Sal. Acid in PEG 1300 | 0 | A | $H_2O$ |
| 7 | 36% Ur126 (DMAC) | 25% Ind. in PEG 3350 | 1 | B(down) | 60% Ethanol in $H_2O$ |
| 8 | 36% Ur126 (DMAC) | 50% Nalb—HCl in 3.6% Ur (DMAC) | ¼ | B(down) | 60% Ethanol in $H_2O$ |
| 9 | 36% Ur126 (DMAC) | 50% Nalb—HCl in 3.6% Ur (DMAC) | ¼ | B(down) | 60% Ethanol in $H_2O$ |
| 10 | 36% Ur126 with 15% PVP40 (DMAC) | 25% Nalb—HCl in 1.8% Ur126 in DMAC | ¼ | B(down) | 60% Ethanol in $H_2O$ |
| 11 | 36% (Ur126 + 25% PVP-15)(DMAC) | 25% Nalb—HCl in 1.8% Ur126 in DMAC | ¼ | B(down) | 60% Ethanol in $H_2O$ |
| 12 | 36% Ur126 (DMAC) | 25% Nalb—HCl in 1.8% Ur126 in DMAC | ¼ | B(down) | 60% Ethanol in $H_2O$ |
| 13 | 15% Elvanol HV ($H_2O$) | 50% PPA in 2% Elvanol in $H_2O$ | 0 | B(down) | 60% Ethanol in $H_2O$ |
| 14 | 20% EVA 150 (THF) | 25% Theo in 3.6% Ur126 (DMAC) | ¼ | B(down) | 60% Ethanol in $H_2O$ |
| 15 | 36% (Ur126 + 25% PVP-15)(DMAC) | 25% Theo in 3.6% Ur126 (DMAC) | 0 | B(down) | 60% Ethanol in $H_2O$ |
| 16 | Polypropylene | 33% Theo 325 mesh in 3.6% Ur126 (DMAC) | Not spun (encapsulated in previously prepared tube) | | |
| 17 | 36% Ur126 | 50% CM in 3.6% Ur126 (DMAC) | 1 | B(down) | 80% Acetone in $H_2O$ |
| 18 | 36% (Ur126: PVP-15,1:1) | 33% (PPA-Dowex) in 3.6% Ur126 (DMAC) | 0 | B(up) | Deionized Distilled Water |

A = Quench tube and rotating piddle bucket (coagulant flows in direction spun)
B = Quench tube bath (stationary)

In vitro dissolution rates of drug-filled hollow tubes whose preparation is shown in Table I were carried out by one of two procedures. One is a standard procedure described in the U.S. Pharmacopeia XXI, page 1243 (1985). This procedure uses a 1 liter glass vessel immersed in water at 30° C. or 37° C. and filled with a vary depending on the rate of release of the drug (2-100 hours). Time should be long enough to allow significant ($\sim >50\%$) release of drug.

The in vitro dissolution procedures of Table I hollow tubes are shown in Table II along with the characteristics of the tubes. The dissolution results are discussed after Table II.

TABLE II

Drug-encapsulated Thin Tubular Membranes And Dissolution Rates

| Ex. No. | Membrane Sheath | Drug & Susp. Agent | Tube Length | Tube Dia. (OD mm.) | Char. | Drug Loading Ult. % of Total | Dissol. Proc. |
|---|---|---|---|---|---|---|---|
| 1 | Ur126 | 3% Theo. in PG | 1" (2.54 cm) | 1.5 | Closed ends 70% Lumen Dia. | 2% | USP 30° C./ 50 rpm[1] |
| 2 | Ur126 | 10% sal. acid in PG | 1" (2.54 cm) | 1.5 | Closed ends 70% Lumen Dia. | 6.9% | USP 30° C./ 50 rpm[1] |
| 3 | Ur126 | 3% Theo. in PG | 1" (2.54 cm) | 1.5 | Closed ends 60% Lumen Dia. | 2% | rot. bottle 37° C./ 15 rpm[1] |
| 4 | Ur126 | 30% sal. acid in PEG 740 | 1" (2.54 cm) | 3.6 | Closed ends 67% Lumen Dia. | 12% | rot. bottle 30° C./ 15 rpm[1] |
| 5 | Ur126 | 30% sal. acid in PEG 1000 | 1" (2.54 cm) | 3.0 | Closed ends 33% Lumen Dia. | 22% | rot. bottle 30° C./ 15 rpm[1] |
| 6 | Ur126 | 30% sal. acid in PEG 1300 | 1" (2.54 cm) | 3.0 | Closed ends 33% Lumen Dia. | 20.2% | rot. bottle 30° C./ 15 rpm[1] |
| 7 | Ur126 | 25% Ind. in PEG 3350 | 1" (2.54 cm) | 2.3 | Closed ends 33% Lumen Dia. | 17% | USP 37° C./ 25 rpm[1] |
| 8 | Ur126 | 50:3.6 Nalb—HCl: Ur126 | 1" (2.54 cm) | 1.8 | Closed and open 82% Lumen Dia. | 56% | USP 37° C./ 50 rpm[2] |
| 9 | Ur126 | 50:3.6 Nalb—HCl: Ur126 | ½", 1" (1.27, 2.54 cm) | 1 | Open —50% Lumen Dia. | 39.8% | USP 37° C./ 50 rpm[2] |
| 10 | Ur126 & 15% PVP-40 | 25:1.8 Nalb—HCl: Ur126 | 1" (2.54 cm) | 1 | Open and closed 50% Lumen Dia. | 40% | USP 37° C./ 50 rpm[2] |
| 11 | Ur126 & 25% PVP-15 | 25:1.8 Nalb—HCl: Ur126 | 1" (2.54 cm) | 1 | Open and closed 67% Lumen Dia. | 56% | USP 37° C./ 50 rpm[2] |
| 12 | Ur126 | 25:1.8 Nalb—HCl: Ur126 | 1" (2.54 cm) | 1 | Open and closed 74% Lumen Dia. | 66% | USP 37° C./ 50 rpm[2] |
| 13 | Elvanol HV | 50:2 PPA: Elvanol HV | 1" (2.54 cm) | 0.8 | Closed ends 40% Lumen | 28% | USP 37° C./ 100 rpm[2] |
| 14 | EVA 150 | 25:3.6 Theo:Ur126 | 1" (2.54 cm) | 0.8 | Closed ends 35% Lumen | 30% | USP 37° C./ 100 rpm[2] |
| 15 | Ur126 & 25% PVP-15 | 25:3.6 Theo: Ur126 | 1" (2.54 cm) | 1.2 | Closed ends 40% Lumen | 51% | USP 37° C./ 100 rpm[2] |
| 16 | Polypropylene | 33:3.6 Theo: Ur126 | 1" (2.54 cm) | 1.2 | Closed ends 37% Lumen | 25% | USP 37° C./ 100 rpm[2] |
| 17 | Ur126 | 50:3.6 CM:Ur126 | ⅛", ½" (0.32 cm, 1.27 cm) | 0.9 | Open ends 75% Lumen | 28% | USP 37° C./ 100 rpm[2] |
| 18 | 1:1 Ur126: PVP-15 | 33:3.6 PPA-Dowex Ur126 | ⅛", ¼", ½" (0.32, 0.64, 1.27 cm) | 0.68 | Open Ends 86% Lumen | 57% | USP 37° C./ 100 rpm[3] |

[1] 0.05 M pH 7.4 phosphate buffer
[2] distilled water
[3] 0.1 NHCl

The drug release patterns obtained with the pharmaceutical compositions of this invention can be further understood by reference to the following examples in which temperatures are in degrees centigrade.

EXAMPLE 1

The dissolution of theophylline from hollow porous polyurethane tubes containing 2% theophylline by weight was determined in pH 7.4 phosphate buffer at 30° C. using the USP dissolution procedure. The tubes were prepared by encapsulating a 3% suspension of theophylline in propylene glycol in polyurethane 126 tubes prepared to have a 1.5 mm outside diameter with a 70% lumen diameter. The drug encapsulated tubes were cut in one inch lengths and both ends were closed. The dissolution bath was stirred at 50 rpm. During the first hour, about 25% of the theophylline was released, followed by a sustained release with about 80% of the total theophylline being released by 11 hours.

EXAMPLE 2

The dissolution of salicylic acid from hollow porous polyurethane tubes containing 6.9% salicylic acid by weight was determined in pH 7.4 phosphate buffer at 30+ C. using the USP dissolution procedure. The tubes were prepared by encapsulating a 10% suspension of salicylic acid in propylene glycol in poyurethane 126 tubular membranes prepared to have a 1.5 mm outside diameter with a 70% lumen diameter. The tubes were cut to one inch lengths and both ends were closed. The dissolution bath was stirred at 50 rpm. Rapid release of 60% of the salicylic acid was observed during the first hour, followed by complete release over 3 hours.

EXAMPLE 3

The dissolution of theophylline from hollow porous polyurethane tubes containing 2% theophylline by weight was determined in pH 7.4 phosphate buffer at 37° C. using the rotating bottle sustained release apparatus equipped with 50 ml bottles. The tubes were prepared by encapsulating a 3% suspension of theophylline in propylene glycol in polyurethane 126 tubular membranes prepared to have a 1.5 mm outside diameter with a 60% lumen diameter. The tubes were cut in one inch lengths and both ends were closed. The bottles were tumbled in the constant temperature bath at 10 rpm. During the first ½ hour, about 40% of the theophylline was released, followed by more constant release to give complete dissolution over 4 hours.

EXAMPLE 4

The dissolution of salicylic acid from hollow porous polyurethane tubes containing 12% salicylic acid by weight was determined in pH 7.4 phosphate buffer at 30+ C. using the rotating bottle sustained release apparatus equipped with 50 ml bottles. The drug encapsulated tubes were prepared by encapsulating a 30% suspension of salicylic acid in polyethylene glycol 740 in polyurethane 126 tubes prepared to have a 3.6 mm outside diameter with a 67% lumen diameter. The tubes were cut in one inch lengths with both ends closed. The bottles were tumbled in the constant temperature bath at 15 rpm. During the first ½ hour, about 30% of the salicylic acid was released, followed by more constant release of 95% of the total salicylic acid over 6 hours.

EXAMPLE 5

The dissolution of salicylic acid from hollow porous polyurethane tubes containing 22% salicylic acid by weight was determined in pH 7.4 phosphate buffer at 30° C. using the rotating bottle sustained release apparatus equipped with 50 ml bottles. The tubes were prepared by encapsulating a 30% suspension of salicylic acid in polyethylene glycol 1000 in polyurethane 126 membranes prepared to have a 3.0 mm outside diameter and a 33% lumen diameter. The tubes were cut in one inch lengths with both ends closed. The bottles were tumbled in the constant temperature bath at 15 rpm. During the first ½ hour, about 35% of the salicylic acid was released, followed by more constant release of 95% of the total salicylic acid over 6 hours.

EXAMPLE 6

The dissolution of salicylic acid from hollow porous polyurethane tubes containing 20.2% salicylic acid by weight was determined in pH 7.4 phosphate buffer at 30° C. using the rotating bottle sustained release apparatus equipped with 50 ml bottles. The tubes were prepared by encapsulating a 30% suspension of salicylic acid in polyethylene glycol 1300 in polyurethane tubes prepared to have a 3.0 mm outside diameter and a 33% lumen diameter. The drug loaded tubes were cut in one inch lengths with both ends closed. The bottles were tumbled in the constant temperature bath at 15 rpm. during the first ½ hour, about 40% of the salicylic acid was released, followed by more constant release of 78% of the total salicylic acid over 6 hours.

EXAMPLE 7

The dissolution of incomethacin from hollow porous polyurethane tubes containing 17% indomethacin by weight was determined in pH 7.4 phosphate buffer using the USP dissolution procedure at 37° C. The tubes were prepared by encapsulating a 25% suspension of indomethacin in polyethylene glycol 3350 in polyurethane 126 tubular membranes prepared to have a 2.3 mm outside diameter with a 33% lumen diameter. The drug loaded tubes were cut in one inch lengths with both ends closed. The dissolution bath was stirred at 25 rpm. During the first ½ hour, about 42% of the indomethacin was released, followed by more constant release of about 85% of the total indomethacin over 11 hours.

EXAMPLE 8

The dissolution of nalbuphine hydrochloride from hollow porous polyurethane tubes containing 56% nalbuphine hydrochloride by weight was determined in distilled water using the USP dissolution procedure at 37° C. The tubes were prepared by encapsuating a mixture of 50 parts nalbuphine hydrochloride to 3.6 parts polyurethane 126 in polyurethane 126 tubular membranes prepared to have a 1.8 mm outside diameter with a 82% lumen diameter. The drug encapsulated tubes were cut in one inch lengths with either both ends closed or both ends left open. The dissolution bath was stirred at 50 rpm. The open-ended tubes showed almost constant release of nalbuphine hydrochloride with complete release over 100 hours. The closed-ended tubes showed almost constant release of nalbuphine hydrochloride; however, only about 25% of the total nalbuphine hydrochloride had been released after 100 hours.

EXAMPLE 9

The dissolution of nalbuphine hydrochloride from hollow porous polyurethane tubes containing 39.8% nalbuphine hydrochloride by weight was determined in distilled water using the USP dissolution procedure at 37° C. The tubes were prepared by encapsulating a mixture of 50 parts nalbuphine hydrochloride to 3.6 parts polyurethane 126 in polyurethane 126 tubes prepared to have a 1 mm outside diameter and a 50% lumen diameter. The tubes were cut in one inch and in ½ inch lengths, giving tubular membranes having aspect ratios (length/diameter) of about 25 and 12.5 respectively. The ends of the drug encapsulated tubes were left open. The dissolution bath was stirred at 50 rpm. Both sets of tubes showed virtually constant release of nalbuphine hydrochloride with the tubes with an aspect ratio of 25 resulting in release of about 20% of the total nalbuphine hydrochloride over a 24 hour period, while the tubes with an aspect ratio of 12.5 resulted in about 65% of the total nalbuphine hydrochloride being released over a 24 hour period.

EXAMPLE 10

The dissolution of nalbuphine hydrochloride from hollow porous polyurethane tubes containing 15% polyvinylpyrrolidone and 40% nalbuphine hydrochloride by weight was determined in distilled water using the USP dissolution procedure at 37° C. The tubes were prepared by encapsulating a mixture of 25 parts nalbuphine hydrochloride and 1.8 parts polyurethane 126 in a tube containing 15% polyvinylpyrrolidone 40 in polyurethane 126 prepared to have a 1 mm outside diameter and a 50% lumen diameter. The drug encapsulated tubes were cut to one inch lengths and the ends were either closed or left open. The dissolution bath was stirred at 50 rpm. The open-ended tubes showed an initial release of about 5% of the nalbuphine hydrochloride during the first ½ hour, followed by a sustained release of 40% of the total nalbuphine hydrochloride by 24 hours. The closed-end tubes showed a rapid release of about 4.5% of the nalbuphine hydrochloride during the first 2 hours, followed by a more sustained release of 8% of the total nalbuphine hydrochloride by 24 hours.

EXAMPLE 11

The dissolution of nalbuphine hydrochloride from hollow porous polyurethane tubes containing 25% polyvinylpyrrolidone 15 and 56% nalbuphine hydrochloride by weight was determined in distilled water using the USP dissolution procedure at 37° C. The tubes were prepared by encapsulating a mixture of 25 parts nalbuphine hydrochloride to 1.8 parts polyurethane 126 in a tube containing 25% polyvinylpyrrolidone 15 in polyurethane 126 prepared to have a 1 mm outside diameter and a 67% lumen diameter. The drug encapsulated tube was cut to one inch lengths and the ends were either closed or left open. The dissolution bath was stirred at 50 rpm. the open-ended tubes showed a fairly constant release with about 36% of the total nalbuphine hydrochloride being released in 24 hours. The tubes with the closed ends showed an initial release of about 5% of the nalbuphine hydrochloride during the first ½ hour, followed by sustained release to reach 10% of the total nalbuphine hydrochloride at 24 hours.

EXAMPLE 12

In contrast to the dissolution observed in Example 11a the dissolution of nalbuphine hydrochloride from hollow porous tubes of polyurethane alone, rather than the blended polymers used in Example 11, was found to be much slower. Tubes were prepared which contained 66% nalbuphine hydrochloride by weight by encapsulating a mixture of 25 parts nalbuphine hydrochloride and 1.8 parts polyurethane 126 in polyurethane 126 tubes with a 1 mm outside diameter and a 74% lumen diameter. The drug encapsulated tubes were cut to one inch lengths and the ends were either closed or left open. The dissolution was determined under the same conditions as those used for Example 11. The open-ended tubes resulted in only 4% dissolution of the total nalbuphine hydrochloride at 24 hours, while the closed-ended tubes released only 1.5% of the total nalbuphine hydrochloride at 24 hours.

EXAMPLE 13

The dissolution of phenylpropanolamine hydrochloride from hollow porous Elvanol HV tubes containing 28% phenylpropanolamine hydrochloride by weight was determined in distilled water using the USP dissolution procedure at 37° C. The tubes were prepared by encapsulating a mixture of 50 parts phenylpropanolamine hydrochloride and 2 parts Elvanol HV in an Elvanol HV tube prepared to have an outside diameter of 0.8 mm with a 40% lumen diameter. The drug encapsulated tubes were cut to one inch lengths and the ends were closed. The dissolution bath was stirred at 100 rpm. Complete release of the phenylpropanolamine hydrochloride was observed in the first two hours.

EXAMPLE 14

The dissolution of theophylline from hollow ethylene vinyl acetate tubes containing 30% theophylline was determined in distilled water using the USP dissolution procedure at 37° C. The tubes were prepared by encapsulating a mixture containing 25 parts theophylline to 3.6 parts polyurethane 126 in a tubular membrane of ethylene-vinyl acetate copolymer (33% vinyl acetate by weight) prepared to have an outside diameter of 0.8 mm and a 35% lumen diameter. The drug encapsulated tubes were cut to one inch lengths and the ends were closed. The dissolution bath was stirred at 100 rpm. After an initial release of about 20% of the theophylline during the first ½ hour, a constant release was observed resulting in complete release of the total theophylline by 24 hours.

EXAMPLE 15

The dissolution of theophylline from hollow porous polymethane tubes containing 25% polyvinylpyrrolidone and 51% theophylline by weight was determined in distilled water using the USP dissolution procedure at 37° C. The tubes were prepared by encapsulating a mixture of 25 parts theophylline to 3.6 parts polyurethane 126 in a tubular membrane of polyurethane 126 polyvinylpyrrolidone 15 blend (25% polyvinylpyrrolidone) prepared to have an outside diameter of 1.2 mm with a 40% lumen diameter. The drug encapsulated tubes were cut to one inch lengths and the ends were closed. The dissolution bath was stirred at 100 rpm. After an initial release of 20% of the theophylline in the first 15 minutes a constant release was observed with complete release of the theophylline by 24 hours.

EXAMPLE 16

The dissolution of theophylline from hollow polypropylene tubes with a mean wall porosity of <0.1 mm containing 25% theophylline by weight was determined in water using the USP dissolution procedure at 37° C. The tubes were prepared by encapsulating a mixture containing 33 parts theophylline to 3.6 parts polyurethane 126 in polypropylene tubes prepared to have an outside diameter of 1.2 mm and a 37% lumen diameter. The drug encapsulated tubes were cut to one inch lengths and the ends were closed. The dissolution bath was stirred at 100 rpm. After an initial release of 11% of the theophylline in the first ½ hour, sustained release was observed with 80% of the total theophylline being released by 24 hours.

EXAMPLE 17

The release of chlorpheniramine maleate from hollow porous polyurethane tubes containing 28% chlorpheniramine maleate by weight was determined in distilled water using the USP dissolution procedure at 37° C. The tubes were prepared by encapsulating a mixture containing 50 parts chlorpheniramine maleate to 3.6 parts polyurethane 126 in a polyurethane 126 tubular membrane prepared to have an outside diameter of 0.9 mm and a 75% lumen diameter. The drug encapsulated tubes were cut to lengths of ⅛ inch (0.32 cm) or ½ inch (1.27 cm), giving tubes with an aspect ratio of 1.4 or 5.6 respectively and the ends were left open. The dissolution bath was stirred at 100 rpm. The tubes with an aspect ratio of 1.4 showed an initial release of 22% of the chlorpheniramine maleate in the first ½ hour, followed by a sustained release to provide 85% of the total chlorpheniramine maleate at 8 hours. The tubes with an aspect ratio of 5.6 showed a constant release to provide 23% of the total chlorpheniramine maleate at 8 hours.

EXAMPLE 18

Release of phenylpropanolamine hydrochloride (PPA) from open-ended hollow tubes whose sheath is constructed of a 1:1 blend of urethane 126 and polyvinylpyrrolidone and with aspect ratios of from 4.6, 9.2, and 18.6 were performed in 0.1N HCl and compared to that obtained with the core material. The release pattern for the drug encapsulated tubes was sustained after an initial burst of 2, 3, and 6% (in <½ hour) and at 24 hours was about 42%, 60% and 70% for the small, medium, and low aspect ratio tubes respectively. The core component showed a faster release of PPA with a burst of 30% in <½ hour up to 100% in 20 hours.

What is claimed is:

1. A process for preparing a hollow tube drug delivery system comprising:
   a. extruding a polymer solution or suspension through an annular orifice to provide a tubular membrane having a hollow core;
   b. simultaneously extruding a drug suspended in a polymer solution into the hollow core of the tubular membrane to provide a drug encapsulated tubular membrane system;
   c. passing the system into a non-solvent for the polymers having a density different from that of the system, to coagulate the polymers under conditions to minimize orientation in the tube polymer and to create pores in the tube polymer wall;
   d. removing residual solvent from the system; and
   e. collecting a drug encapsulated, porous polymeric hollow tube.

2. The process of claim 1 wherein the drug encapsulated tubular membrane system from step b. is drawn-down prior to being passed into the non-solvent coagulant.

3. The process of claim 1 wherein the resulting drug encapsulated, porous hollow tube has an outside diameter of about 0.5-10 millimeters.

4. The process of claim 3 wherein the collected tube is cut into lengths in the range of about 0.5 mm to about 2 cm.

5. The process of claim 3 wherein the polymer solution is about 15-40% by weight of a segmented polyurethane(urea derived from polyether glycol soft segments and free of additives in dimethylacetamide or N-methylpyrrolidone.

6. The process of claim 5 wherein polymer solution is about 30-40% by weight of the segmented polyurethane/urea in dimethylacetamide.

7. The process of claim 3 wherein the polymer solution is about 15-25% by weight of a polylactide of number average molecular weight of about 100,000 to 500,000 in dimethylacetamide or a chlorinated solvent.

8. The process of claim 7 wherein polylactide is dissolved in chloroform.

9. The process of claim 3 wherein the polymer solution is about 15-25% by weight of polyvinyl alcohol in water.

10. The process of claim 3 wherein the extrusions of steps a. and b. are downward through an airgap to affect draw-down by gravity, and the non-solvent coagulant has a density less than the density of the drug encapsulated tubular membrane system.

11. The process of claim 3 wherein the drug suspension consists essentially of a drug suspended in a polymer solution.

12. The process of claim 11 wherein the polymer solution is selected from propylene glycol, polyethylene glycol having a molecular weight greater than about 400, about 1-12% by weight of a segmented polyurethane/urea in dimethylacetamide, and about 1-5% by weight of polyvinyl alcohol in water.

13. The process of claim 3 wherein the temperature of the non-solvent coagulant is in the range of about 60° to 180° C. to increase the pore size in the tube polymer wall.

14. The process of claim 3 wherein the extrusions of steps a. and b. and the non-solvent coagulant are at about the same temperature, said temperature in the range of about 15° to 180° C.

15. A process for preparing a hollow tube drug delivery system comprising:
   a. extruding a solution of about 15-40% by weight of a segmented polyurethane/urea derived from polyether glycol soft segments in dimethylacetamide through an annular orifice to provide a tubular membrane having a hollow core;
   b. simultaneously extruding into the hollow core of the tubular membrane a drug suspension consisting essentially of about 3-50% by weight of a drug suspended in a polymer solution selected from propylene glycol, polyethylene glycol having a number average molecular weight greater than about 400, about 1-12% by weight of a segmented polyurethane/urea in dimethylacetamide, and about 1-5% by weight of polyvinyl alcohol in water, to provide a drug encapsulated tubular membrane system;
   c. passing the system after a draw-down into a polymer coagulation bath selected from water, an alkyl alcohol of 1-3 carbon atoms and a mixture thereof, to provide a drug encapsulated porous hollow tube having an outside diameter of about 0.5-10 millimeters;
   d. removing residual solvent from the drug encapsulated, porous hollow tube; and
   e. collecting the resulting tube.

16. The process of claim 15 wherein the drug encapsulated tubular membrane system is extruded downward into the coagulation bath through an airgap to provide a gravity draw-down.

17. The process of claim 16 wherein residual solvent is removed by heating the drug encapsulated, porous hollow tube.

18. The process of claim 17 wherein the tube is collected on a wind-up roll.

19. The process of claim 18 wherein the collected tube is cut into lengths in the range of about 0.5 mm to about 2 cm.

20. The process of claim 19 wherein a plurality of the cut tubes are mixed with a suitable pharmaceutical carrier for oral administration.

21. The process of claim 16 wherein the extrusions of steps a. and b. and the coagulation bath are at about the same temperature in the range of about 15° to 180° C.

* * * * *